(12) United States Patent  (10) Patent No.: US 9,180,301 B2
Maskara et al.  (45) Date of Patent: Nov. 10, 2015

(54) ESTIMATING ELECTROMECHANICAL DELAY TO OPTIMIZE PACING PARAMETERS IN RBBB PATIENTS

(71) Applicant: Cardiac Pacemakers, Inc., St. Paul, MN (US)

(72) Inventors: Barun Maskara, Blaine, MN (US); Qi An, Blaine, MN (US); Pramodsingh Hirasingh Thakur, Woodbury, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/200,175

(22) Filed: Mar. 7, 2014

(65) Prior Publication Data

US 2014/0277239 A1  Sep. 18, 2014

Related U.S. Application Data

(60) Provisional application No. 61/793,552, filed on Mar. 15, 2013.

(51) Int. Cl.
*A61N 1/365* (2006.01)
*A61B 5/0452* (2006.01)
*A61N 1/05* (2006.01)
*A61N 1/368* (2006.01)

(52) U.S. Cl.
CPC .......... *A61N 1/36585* (2013.01); *A61B 5/0452* (2013.01); *A61N 1/0563* (2013.01); *A61N 1/3682* (2013.01)

(58) Field of Classification Search
None
See application file for complete search history.

(56) References Cited

U.S. PATENT DOCUMENTS

| 5,554,177 | A | 9/1996 | Kieval et al. |
| 7,209,786 | B2 | 4/2007 | Brockway et al. |
| 7,953,484 | B2 | 5/2011 | Brockway et al. |
| 8,016,764 | B1 | 9/2011 | Shelchuk |
| 8,041,424 | B2 | 10/2011 | Corbucci |
| 8,060,201 | B2 | 11/2011 | Holmström et al. |
| 8,133,187 | B2 | 3/2012 | Holmstrom et al. |
| 8,204,590 | B2 | 6/2012 | Sambelahvili |
| 2005/0027322 | A1* | 2/2005 | Warkentin ............... 607/17 |
| 2006/0094967 | A1* | 5/2006 | Bennett et al. ........... 600/508 |
| 2006/0293714 | A1* | 12/2006 | Salo et al. .................. 607/9 |
| 2007/0255327 | A1 | 11/2007 | Cho et al. |
| 2008/0288013 | A1 | 11/2008 | Schecter |
| 2009/0254139 | A1 | 10/2009 | Bjorling |
| 2010/0087888 | A1 | 4/2010 | Maskara et al. |
| 2010/0100148 | A1 | 4/2010 | Min et al. |
| 2011/0257696 | A1 | 10/2011 | Holmstrom et al. |
| 2012/0109244 | A1* | 5/2012 | Anderson et al. ......... 607/17 |
| 2012/0253419 | A1* | 10/2012 | Rosenberg et al. ....... 607/25 |
| 2012/0289848 | A1 | 11/2012 | Li |
| 2012/0296228 | A1* | 11/2012 | Zhang et al. ............. 600/513 |
| 2013/0053913 | A1* | 2/2013 | Koh et al. ................. 607/17 |

OTHER PUBLICATIONS

US 7,706,880, 04/2010, Patangay et al. (withdrawn)

* cited by examiner

*Primary Examiner* — Kennedy Schaetzle
(74) *Attorney, Agent, or Firm* — Schwegman Lundberg & Woessner, P.A.

(57) ABSTRACT

Stimulation energy can be provided to stimulate synchronous ventricular contractions. Interval information obtained from a cardiac electrical heart signal and a cardiac mechanical heart signal can be used to determine a right ventricular activation time. The interval information can provide a cardiac stimulation indication.

20 Claims, 7 Drawing Sheets

ESTIMATING ELECTROMECHANICAL DELAY TO OPTIMIZE PACING PARAMETERS IN RBBB PATIENTS

CLAIM OF PRIORITY

This application claims the benefit of priority under 35 U.S.C. §119(e) of U.S. Provisional Patent Application Ser. No. 61/793,552, filed on Mar. 15, 2013, which is herein incorporated by reference in its entirety.

BACKGROUND

A medical device can be implanted in a body to perform one or more tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. Examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system.

In various examples, cardiac rhythm or function management devices can sense intrinsic heart contractions, deliver pacing pulses to evoke responsive heart contractions, or deliver a shock to interrupt certain arrhythmias. In certain examples, one or more of these functions can help improve a patient's heart rhythm or can help coordinate a spatial nature of a heart contraction, either of which can improve cardiac output of blood.

Some cardiac rhythm or function management devices can be configured to deliver energy at or near the right ventricle of a patient's heart to achieve pacing via natural conduction pathways, such as when a patient has right bundle branch block. Various methods for treating patients with right bundle branch block have been proposed. For example, Corbucci. U.S. Pat. No. 8,041,424, entitled CARDIAC RESYNCHRONIZATION THERAPY FOR PATIENTS WITH RIGHT BUNDLE BRANCH BLOCK, refers to an implantable medical device and associated method to deliver cardiac resynchronization therapy in a patient having right bundle branch block by measuring an interval between a right atrial depolarization and a first heart sound and selecting a right atrial-ventricular (AV) pacing interval in response to the measure interval.

Zhang et al. U.S. Patent Application No. 20120296228 entitled HEART SOUNDS-BASED PACING OPTIMIZATION, refers to an implantable medical device configured to receive both heart sound and electrogram signals.

OVERVIEW

Right bundle branch block results from a defect in the heart's electrical conduction system. In a heart suffering from right bundle branch block, the right ventricle is not directly activated by an electrical impulse travelling through the right bundle branch. However, the left ventricle is normally activated by an electrical impulse travelling through the left bundle branch. The result is mechanical dyssynchrony between the right and left ventricles of a heart. A cardiac response to artificial pacing can help alleviate the dyssynchrony. An effective pacing technique can include inducing a pacing event by delivering stimulation to the right ventricle of a patient's heart, producing a synchronous cardiac response.

This document describes, among other things, systems, methods, machine-readable media, or other techniques that can include detecting at least one of a right ventricular activation or a right ventricular electrostimulation, distinguishing a pulmonary valve opening from other information associated with an S1 heart sound, measuring a first time interval between the detected right ventricular activation and the subsequent pulmonary valve opening time occurring during the same cardiac cycle, and delivering electrostimulations to the heart using the first time interval between the detected right ventricular activation and the subsequent pulmonary valve opening time occurring during the same cardiac cycle.

The techniques can involve detecting intrinsic and non-intrinsic cardiac activity, such as using a plurality of sensors to detect electrical or mechanical cardiac events. Using timing information associated with pacing and detected cardiac activity, an interval can be determined and optimal pacing intervals can be provided in an automated fashion, such as without analysis of QRS waveforms.

The present inventors have recognized, among other things, that a problem to be solved can include providing cardiac resynchronization therapy to a subject at optimal pacing timing intervals. Resynchronization therapy can be provided by delivering pacing pulses to one or both heart chambers. In an example, the present subject matter can provide a solution to the optimization problem, such as by measuring time intervals between electrical and sensed mechanical events. A single sensor can be used to provide cardiac activity information and related interval information. The interval information can be compared to a threshold value to provide cardiac information, including optimal pacing timing interval information. Alternatively, the pacing timing interval that results in the shortest or longest mechanical activity interval can be identified as the optimal pacing timing interval.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Stimulation energy can be provided to a right ventricle to achieve synchronous, coordinated cardiac contractions. Interval information, such as an interval between a right ventricle (RV) pacing pulse and subject mechanical activity can provide cardiac stimulation information useful for therapy. For example, interval information can be used to time a subsequent pace event.

A natural conduction pathway of the heart that can activate cardiac contractions originates in the sinoatrial (SA) node in the right atrium of the heart. Intrinsic electrical impulses, generated at the SA node, can trigger the atria to contract. From the SA node, a conduction pathway leads electrical impulses to the atrioventricular (AV) node, located between the atrium and the ventricle. Following a delay at the AV node, conduction can continue through the His-bundle to the left and right bundle branches, then to the Purkinje fibers and the apex of the heart, and finally up and around to the ventricular myocardium to produce a coordinated cardiac contraction, such as of both the left and right ventricles.

In an example, cardiac resynchronization therapy can pace the heart at a timing interval to produce a coordinated synchronous cardiac contraction, such as of both the left and right ventricles. Such cardiac resynchronization therapy can be more effective than traditional therapies when pacing timing intervals are optimized. In an example, a cardiac response to a pacing event can provide information useful for adjusting pacing intervals, resulting in improved cardiac pacing.

Figure 1:
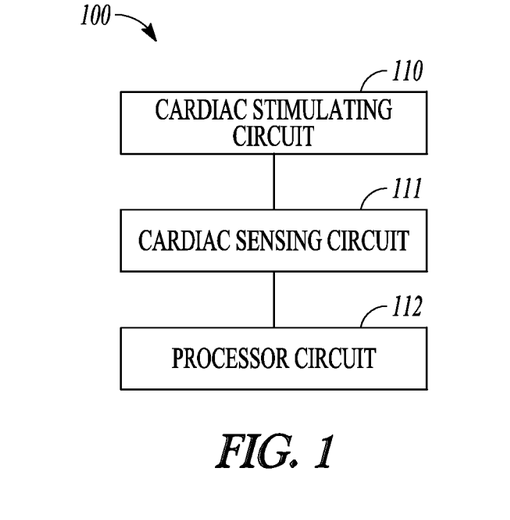
FIG. 1 illustrates generally an example of a system including a cardiac stimulating circuit, a cardiac sensing circuit, and a processor circuit.

FIG. 1 illustrates generally an example of a system 100 that can include a cardiac stimulating circuit 110, a cardiac sensing circuit 111, and a processor circuit 112. In an example, the cardiac stimulating circuit 110 can be configured to generate a stimulation energy configured to invoke cardiac depolarization of the right ventricle. In an example, the stimulation energy can be configured to provide right ventricle stimulation.

Right ventricle stimulation can include, for example, right ventricular apical pacing, right ventricular outflow tract pacing, right ventricular septum pacing, direct His-bundle pacing, or one or more other pacing sites.

In an example, the cardiac sensing circuit 111 can be configured to receive electrical information from the heart, for example, over at least a portion of the cardiac cycle. In an example, the electrical information can include an electrical cardiogram (ECG) signal (e.g., an evoked response, a subcutaneous ECG, or other), an electrical signal from a heart sound sensor such as a microphone, an electrical signal from an accelerometer configured to provide an indication of mechanical cardiac activity, an electrical signal from a pressure sensor configured to provide an indication of a pressure, such as a right ventricle pressure (RVP), or one or more other electrical signals indicative of cardiac information (e.g., thoracic impedance).

The processor circuit 112 can be configured to determine a characteristic of the received electrical information from the heart over at least a portion of the cardiac cycle using the received electrical information. In an example, the characteristics can include at least one of:

(1) a width, amplitude, slope, or latency of a QRS complex;

(2) a pressure;

(3) an indication of mechanical motion provided by an accelerometer; or (4) an impedance.

In an example, one or more other characteristics can be used, such as a measure of contractility, synchrony, or cardiac output, among others. In an example, characteristics can include QRS axis/polarity or repolarization index information (e.g., T-wave polarity, measures or surrogate measures of repolarization time, etc.), or an indication of QRS axis deviation, such as can be provided by an array of electrodes disposed on or in a body.

Information from the determined characteristics can be used to calculate a time interval. For example, a time interval can be calculated from the time cardiac stimulation energy is provided to mechanical activation of the right ventricle. A second time interval can indicate the time from mechanical activation of the right ventricle, to the time at which the right ventricle reaches a maximum pressure. Numerous additional or alternative other intervals can be measured, such as using any number of electrode and sensor configurations described in FIGS. 3 and 4.

In an example, the processor circuit 112 can be configured to provide a cardiac stimulation indication using the determined interval, such as using a detected change in the determined interval, or comparing the interval to a threshold. For example, the processor circuit 112 can provide a cardiac stimulation indication using a cardiac stimulation metric. In an example, the cardiac stimulation indication can be used to modify pacing or resynchronization therapy, such as using the systems and methods described below.

In an example, the processor circuit 112 can be configured to report (or make available) one or more cardiac stimulation indications to an external module (e.g., an external programmer, directly to a clinician's handheld mobile device, email, etc.). In an example, the processor circuit 112 can be configured to provide a cardiac stimulation indication for a plurality of cardiac cycles, count or store one or more of the results from the classification, such as in a histogram, and, when the interval is below a threshold, the processor can be configured to do one or more of the following:

(1) provide an alert to an external module;

(2) reduce the stimulation energy to save power;

(3) increase the stimulation energy (e.g., the pacing threshold) to the right ventricle;

(4) switch to a different pacing configuration (e.g., different pacing waveform, site, etc.); or (5) initiate a test to determine the interval over a set period of time.

In certain examples, the obtained intervals can be trended and the trending can be provided to an external module and displayed to the user.

In an example, the processor circuit 112 can be configured to increase the stimulation energy (e.g., the pacing threshold) to decrease the interval between stimulation and mechanical activation of the right ventricle. In certain examples, the stimulation energy can be increased after a time period (e.g., a number of hours, days, etc.), after a number of cardiac cycles, after a number of interval determinations, among other times.

Figure 2:
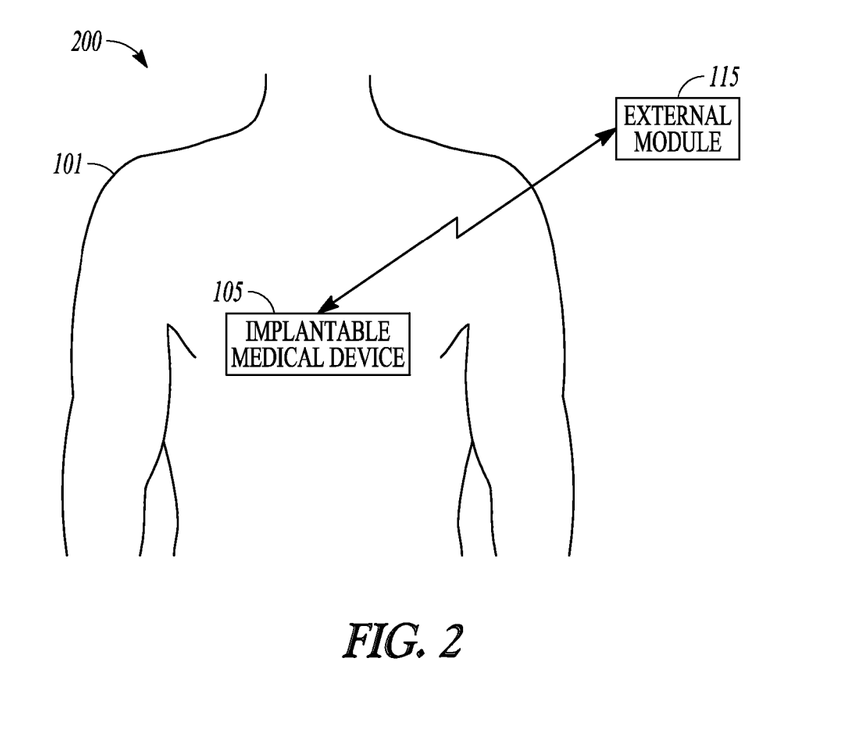
FIG. 2 illustrates generally an example of a system including an implantable medical device (IMD) in a subject, the IMD wirelessly coupled to an external module.

FIG. 2 illustrates generally an example of a system 200 including an ambulatory or implantable medical device (IMD) 105 in a subject 101, the IMD 105 wirelessly coupled to an external module 115. In an example, the IMD 105 can include one or more of the cardiac stimulating circuit 110, the cardiac sensing circuit 111, or the processor circuit 112. In certain examples, a portion of the functionality of one or more of the cardiac stimulating circuit 110, the cardiac sensing circuit 111, or the processor circuit 112 can occur in the IMD 105, and another portion elsewhere (e.g., in an external component, such as a 12-lead ECG).

In an example, the IMD 105 can include a pacemaker, a defibrillator, or one or more other implantable medical devices. In an example, the IMD 105 can include an antenna configured to provide radio-frequency or other communication between the IMD 105 and the external module 115, or other external device. In an example, the external module 115 can include an antenna. In an example, the external module 115 can include a local medical device programmer or other local external module, such as within wireless communication range of the IMD 105 antenna. The external module 115 can include a remote medical device programmer or one or more other remote external modules (e.g., outside of wireless communication range of the IMD 105 antenna, but coupled to the IMD 105 using a local external device, such as a repeater or network access point). In an example, the external module 115 can be configured to send information to or receive information from the IMD 105. The information can include medical device programming information, subject data, device data, or other instructions, alerts, or other information. In an example, the external module 115 can be configured to display information (e.g., received information) to a user. Further, the local programmer or the remote programmer can be configured to communicate the sent or received information to a user or physician, such as by sending an alert, for example, via email of the status of the subject 101 or the system 200 components.

Figure 3:
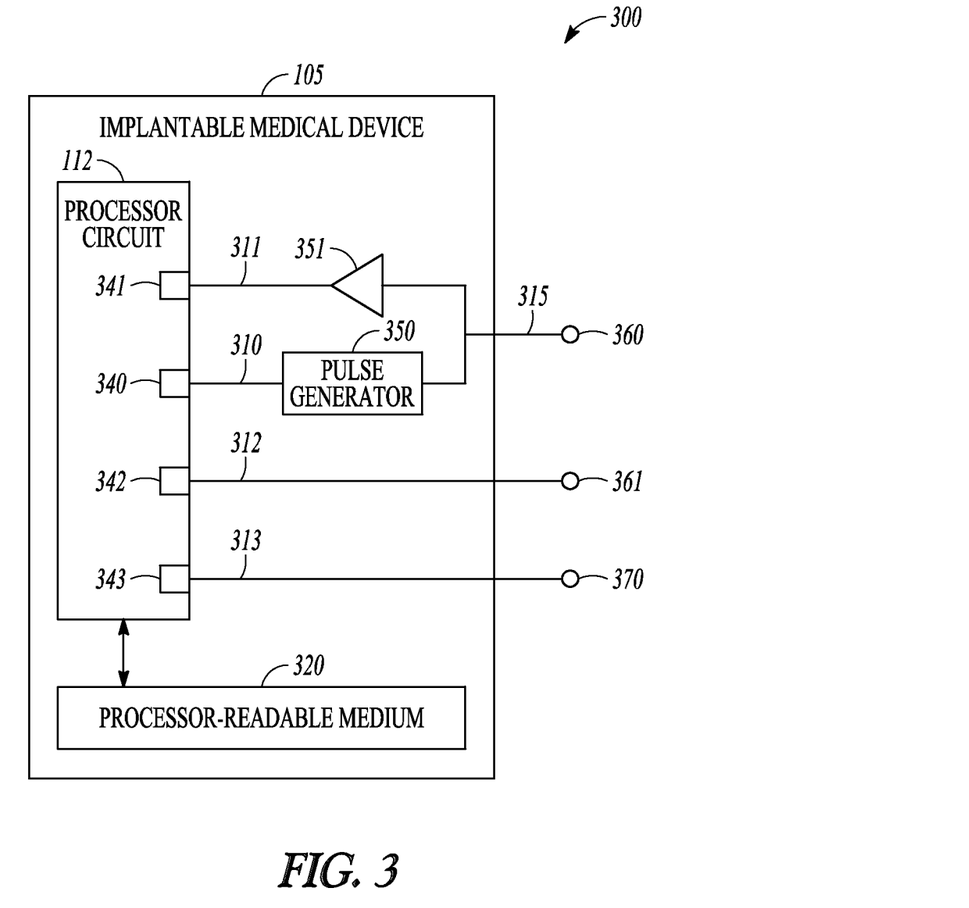
FIG. 3 illustrates generally an example of a portion of an IMD for delivering cardiac therapy and monitoring cardiac activity.

FIG. 3 illustrates generally an example of a system 300 for delivering stimulation energy to a subject or sensing a subject response. In an example, the system 300 can include an IMD 105, the IMD 105 including systems configured to deliver stimulation energy to a subject, or receive information about physiological activity. In an example, the system 300 can include several pacing and sensing channels, such as a right ventricular pacing channel 310, a left ventricular pacing channel 312, a right ventricular sensing channel 311, or a sensor sensing channel 313. In an example, the system 300 can include a processor circuit 112, and a processor-readable medium 320, such as can be accessed using the processor circuit 112.

In an example, the processor circuit 112 can include a plurality of data inputs and outputs. For example, a first data output 340 can be coupled to the right ventricular pacing channel 310, such as to provide control information to a pulse generator 350. The pulse generator 350 can be coupled to an electrode 360 disposed on a lead 315 or elsewhere. A first data input 341 can be coupled to the right ventricular sensing channel 311, such as to receive, via a sense amplifier 351, an electrical signal from the electrode 360. In an example, the electrode 360 can be configured to be located in any region of the right ventricle.

In an example, a second data output 342 can be coupled to the left ventricular pacing channel 312, such as can be coupled to an electrode 361 via lead 312. A second data input 343 can be coupled to a first sensor 370, such as a pressure sensor configured to be disposed in the right ventricle, such as to measure right ventricle pressure. In an example, the processor circuit 112 can receive pressure information via an electrical signal and can interpret the pressure signal, such as using instructions provided on the processor-readable medium 320.

In an example, the system 300 and the IMD 105 can include several additional pacing or sensing channels, such as an atrial pacing channel, an internal thoracic pacing or sensing channel configured to couple the processor circuit 112 to an internal thoracic location external to the heart (e.g., through one or more leads, electrodes, pulse generators, or sense amplifiers), or one or more other atrial or ventricular pacing or sensing channels, among others. The system 300 can include several additional sensing channels, configured to receive information from sensors such as accelerometers, pressure sensors, or electrodes configured to measure electric field information. In an example, the IMD 105 can include one or more other right or left ventricular sensing or pacing channels, such as a right ventricular apex backup pacing channel.

In the example of FIG. 3, the processor circuit 112 can be an implantable component, an external component, or a combination or permutation of an implantable processor and an external processor. In an example, if at least a portion of the processor circuit 112 includes an external processor, then the processor circuit 112 can be configured to be communicatively coupled (such as via telemetry, RF, or other communication protocol) with the remaining implantable components such as the sense amplifier 351, the pulse generator 350, or the processor-readable medium 320. In an example, the implantable processor can be configured to have reduced or minimal functionality or power consumption. In some examples, it can be advantageous for the processor circuit 112 to include an external processor for computing complex operations or to store large amounts of information. In an example, the processor circuit 112 can include a microcontroller, a microprocessor, a logic circuit, or other processor. In an example, the cardiac stimulation circuit 110 can include the pulse generator 350, and the cardiac sensing circuit 111 can include the sense amplifier 351.

Figure 4:
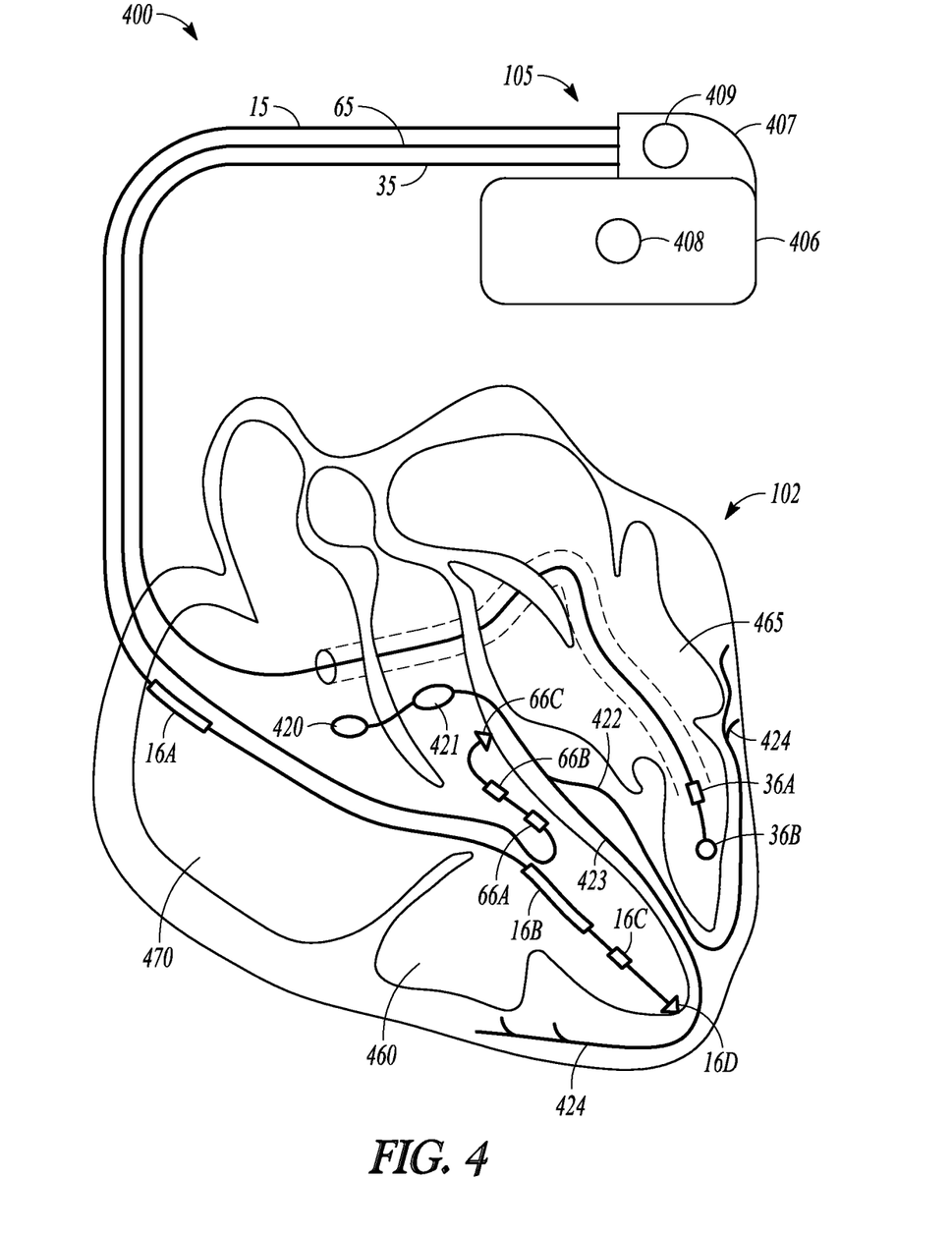
FIG. 4 illustrates generally an example of a system or portion of a system for delivering cardiac therapy or monitoring cardiac activity.

FIG. 4 illustrates generally an example of a system 400 including an IMD 105, a right ventricular apex lead 15, a left ventricular lead 35, and a right ventricular septum lead 65. The IMD 105 can include a housing 406 (or CAN) and a header 407. In an example, at least a portion of the exterior of the housing 406 or the header 407 can include an electrode, such as a housing can electrode 408, or a header electrode 409.

The right ventricular apex lead 15 can include a first electrode 16A configured to be located in the superior vena cava of a heart 102, and a second electrode 16B, a third electrode 16C, and a fourth electrode 16D configured to be located in the right ventricle 460 of the heart 102. In an example, the first electrode 16A can include a proximal defibrillation coil electrode, or the second electrode 16B can include a distal defibrillation coil electrode, such as can be configured to deliver a high energy shock (e.g., 0.1 Joule or greater) to the heart.

The left ventricular lead 35 can include a fifth electrode 36A and a sensor 36B configured to be located in, on, or near the left ventricle 465 of the heart 102, such as within the coronary vasculature. In an example, the sensor 36B can include a distal pacing or sensing electrode, or a pressure sensor. The right ventricular septum lead 65 can include a sixth electrode 66A, an seventh electrode 66B, and a eighth electrode 66C configured to be located along the septum in the right ventricle 460 of the heart 102. In an example, the right ventricular septum lead 65 can be configured to provide His-bundle pacing along the septum wall. In an example, the housing can electrode 408 can be electrically coupled to at least one other electrode (e.g., the first electrode 16A), or the housing can electrode 408 can be electrically isolated from other electrodes and capable of independent control. In an example, the first electrode 16A through the eighth electrode 66C can include at least one of a coil-type electrode, a ring-type electrode, or a tip electrode.

In an example, the right ventricular apex lead 15 can be configured to electrically couple the IMD 105 to at least one of the right ventricle 460, the right atrium 470, or the superior vena cava using at least one electrode (e.g., the first electrode 16A, the second electrode 16B, the third electrode 16C, or the fourth electrode 16D), the left ventricular lead 35 can be configured to electrically couple the IMD 105 to the left ventricle 465 using at least one electrode (e.g., the fifth electrode 36A or the sensor 36B), or the right ventricular septum lead 65 can be configured to electrically couple the IMD 105 to the interventricular septum using at least one electrode (e.g., the sixth electrode 66A, the seventh electrode 66B, or the eighth electrode 66C). In an example, at least one of the second electrode 16B, the third electrode 16C, or the fourth electrode 16D, can be configured to be located in, on, or near a right apical region of the heart 102. In other examples, the fifth electrode 36A or the sensor 36B can be configured to be located in, on, or near a left apical region of the heart 102 or a left ventricular free lateral wall of the heart 102. In an example, a cardiac rhythm management device capable of delivering defibrillation energy can include a shocking electrode, such as the first electrode 16A, electrically tied or coupled to the housing can electrode.

FIG. 4 illustrates several of the natural conduction systems of the heart. For example, the eighth electrode 66C is located near the His-bundle 421 and the AV node 420. The His-bundle is coupled to the left branch bundle 422 and the right branch bundle 423. Each of the left and right branch bundles leads to the Purkinje fibers 424 near the apex of the heart 102. In an example, the system 400 can include a plurality of sensors configured to detect cardiac activity, such as an intrinsic cardiac contraction via Purkinje fiber conduction. For example, the system 400 can include an accelerometer, or other sensor configured to detect heart sound information. The system 400 can include one or more pressure sensors, such as can be disposed in one of the atria or ventricles, or a vein or sinus, such as to provide timing information regarding the opening and closing of the heart valves. In an example, a pressure sensor disposed in the coronary vein can indirectly provide information about left ventricular pressure. In an example, the pressure sensors can be wirelessly coupled to the IMD 105.

Figure 5:
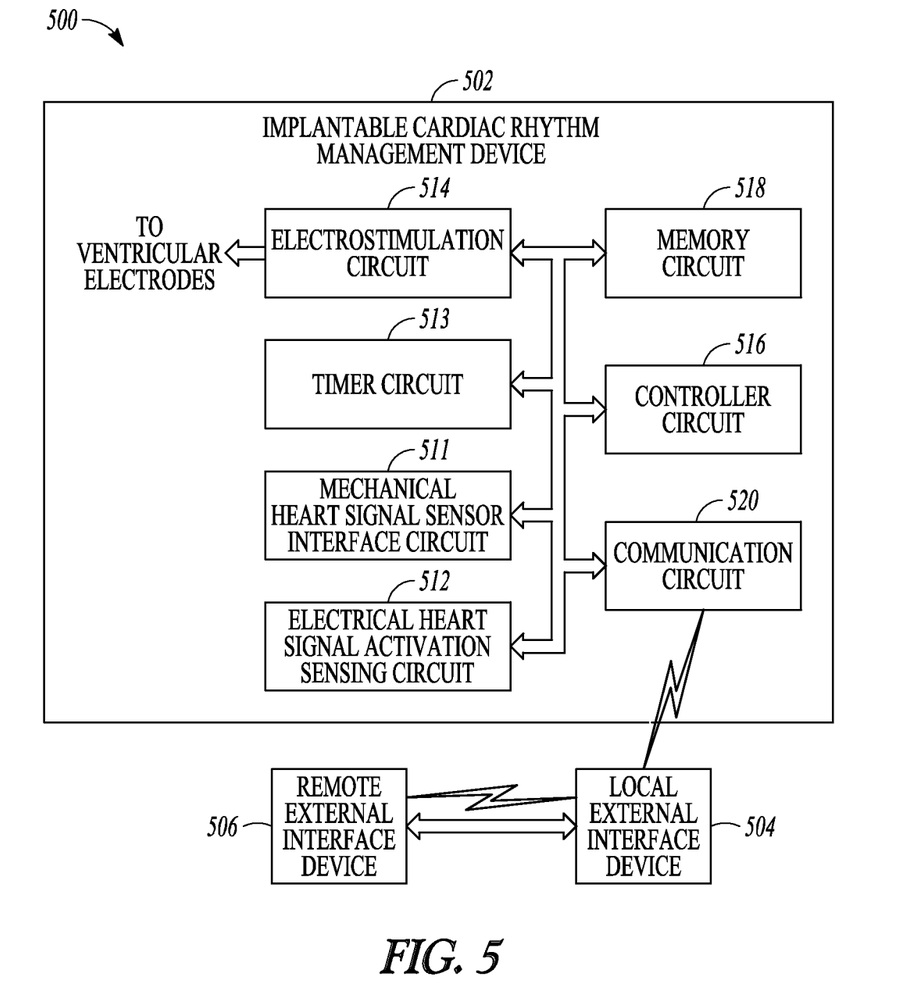
FIG. 5 illustrates generally an example of portions of a cardiac function management system and an environment in which it is used.

FIG. 5 illustrates generally, at 500, an example of portions of a cardiac function management system and an environment in which it can be used. In an example, the system 500 can include an ambulatory medical device, such as an external (e.g., wearable) medical device or an implantable cardiac rhythm or function management device 502, a local external interface device 504, and an optional remote external interface device 506.

In an example, the implantable device 502 can include a mechanical heart signal sensor interface circuit 511, an electrical heart signal activation sensing circuit 512, a timer circuit 513, a heart electrostimulation circuit 514, a memory circuit 518, a controller circuit 516, and a communication circuit 520.

The mechanical heart signal sensor interface circuit 511 can include a subcutaneous sensor, such as an accelerometer or an acoustic transducer to obtain a mechanical heart signal. The mechanical heart signal sensor interface circuit 511 can be configured to detect at least one of a right ventricular activation or a right ventricular electrostimulation, and to determine therefrom a corresponding right ventricular activation time. The mechanical heart signal sensor interface circuit 511 can be configured to receive information, including a mechanical heart signal, such as by detecting a change in one or more of left ventricular pressure, right ventricular pressure, left atrial pressure, right atrial pressure, systemic arterial pressure and pulmonary artery pressure, indicative of mechanical cardiac activity, for example. The mechanical heart signal sensor interface circuit 511 can be configured to receive information, including a mechanical heart signal, such as by detecting a change in blood flow rate or blood perfusion and/or detecting ventricular motion or acceleration, indicative of mechanical cardiac activity, for example. The mechanical heart signal sensor interface circuit 511 can be configured to receive information, including a mechanical heart signal, such as by transthoracically or intrathoracically detecting a change in ventricular impedance indicative of mechanical cardiac activity, for example.

The mechanical heart signal sensor interface circuit 511 can include a right ventricular impedance feature detector circuit. The right ventricular impedance feature detector circuit can be configured to detect a right ventricular impedance feature and provide a corresponding right ventricular impedance feature detection time. The mechanical heart signal sensor interface circuit 511 can include a left ventricular impedance feature detector circuit. The right ventricular impedance feature detector circuit can be configured to detect a left ventricular impedance feature and to provide a corresponding left ventricular impedance feature detection time.

The mechanical heart signal sensor interface circuit 511 can include a filter circuit. The filter circuit can be configured to use information about the right ventricular and left ventricular impedance feature detection times to filter a signal to extract the pulmonary valve opening information from other information associated with an S1, M1, T1, or S2 heart sound.

The filter circuit can be configured to receive an acoustic signal including at least S1 heart sound information. The filter circuit can be configured to use the right ventricular and left ventricular impedance feature detection times such as to define at least one window of an acoustic signal from which to extract pulmonary valve opening information from other information associated with an S1 heart sound. The filter circuit can be configured to define at least one window in a time-frequency domain.

The electrical heart signal activation sensing circuit 512 can be configured to detect at least one of a right ventricular activation or a right ventricular electrostimulation such as to determine therefrom a corresponding right ventricular activation time.

The timer circuit 513 can be coupled to an electrical heart signal activation sensing circuit 512 and a mechanical heart signal sensor interface circuit 511. The timer circuit 513 can be configured to measure a first time interval between a detected right ventricular activation and a subsequent pulmonary valve opening time occurring during the same cycle. The timer circuit 513 can be configured to measure a time interval between a detected right ventricular activation and a heart sound, such as S1, M1, T1, S2, S3 and S4. The timer circuit 513 can be configured to measure a time interval between a detected right ventricular activation and any heart sound obtained from a fiducial point.

The heart electrostimulation circuit 514 can be coupled to the timer circuit. The heart electrostimulation circuit 514 can be configured to deliver electrostimulations to the heart to synchronize a heart contraction within a heart chamber or between heart chambers. The heart electrostimulation circuit 514 can include at least one operation parameter determined using a first time interval between detected right ventricular activation and the subsequent pulmonary valve opening time occurring during the same cardiac cycle.

A controller circuit 516 can be coupled to a mechanical heart signal sensor interface circuit 511, an electrical heart signal activation sensing circuit 512, a timer circuit 513, a heart electrostimulation circuit 514, such as to receive information from the sensed cardiac signals. The controller circuit 516 can include a signal processor circuit, such as a digital signal processor (DSP) circuit, such as for extracting a template parameter from which a diagnostic indicator can be generated. In an example, the signal processor circuit can include dedicated circuitry for performing one or more signal processing functions, such as convolution in the time-domain or the frequency domain, or signal conversion from the time-domain to the frequency-domain or from the frequency domain to the time-domain.

The controller circuit 516 can be coupled to a heart resynchronization electrostimulation circuit 514 to provide control or triggering signals to trigger timed delivery of the therapy pulses. The controller circuit 516 can be configured to provide control to help permit the therapy to be effectively delivered, such as in combination with one or more other therapies (e.g., bradycardia pacing, antitachyarrhythmia pacing (ATP), cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.).

A memory circuit 518 can be coupled to the controller circuit 516, such as to store control parameter values, physiological data, or other information. A communication circuit 520 can be coupled to the controller circuit 516 to permit radiofrequency (RF) or other wireless communication with an external device, such as the local external interface device 504 or the remote external interface device 506.

Figure 6A:
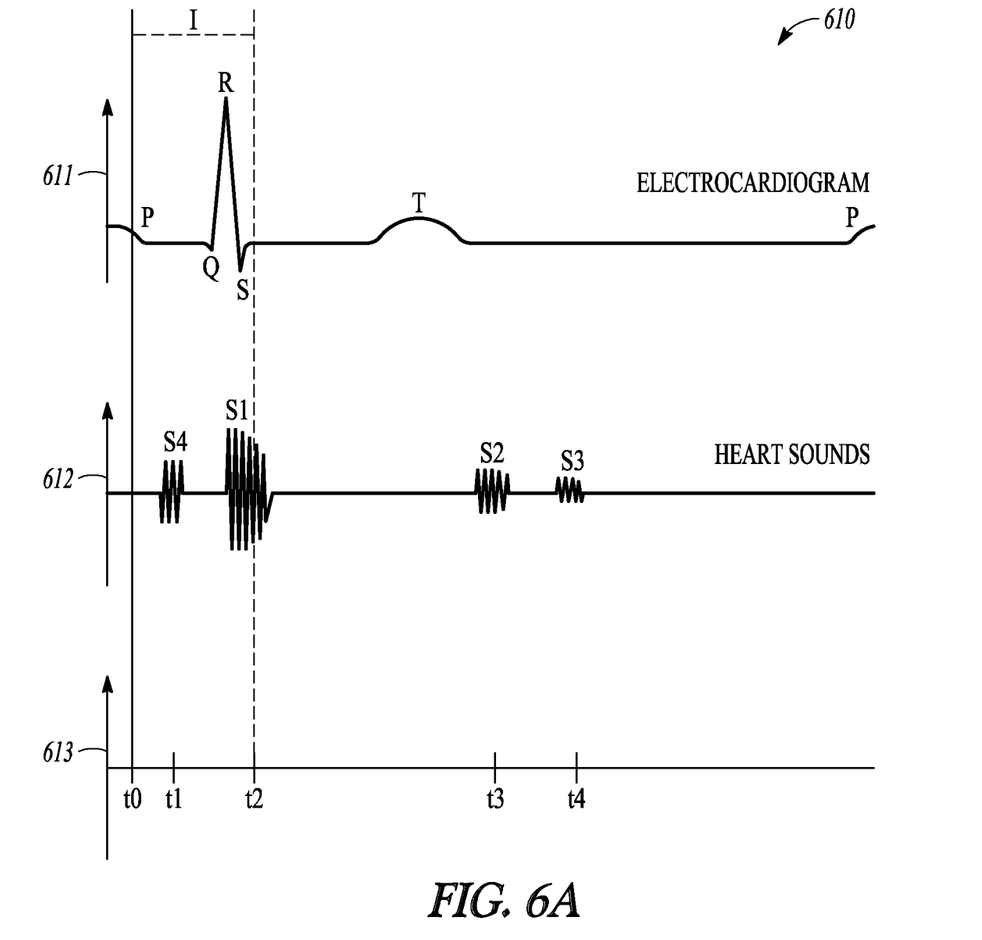
FIGS. 6A-B illustrates generally an example of measuring a time interval using electrical and mechanical signals.
Figure 6B:
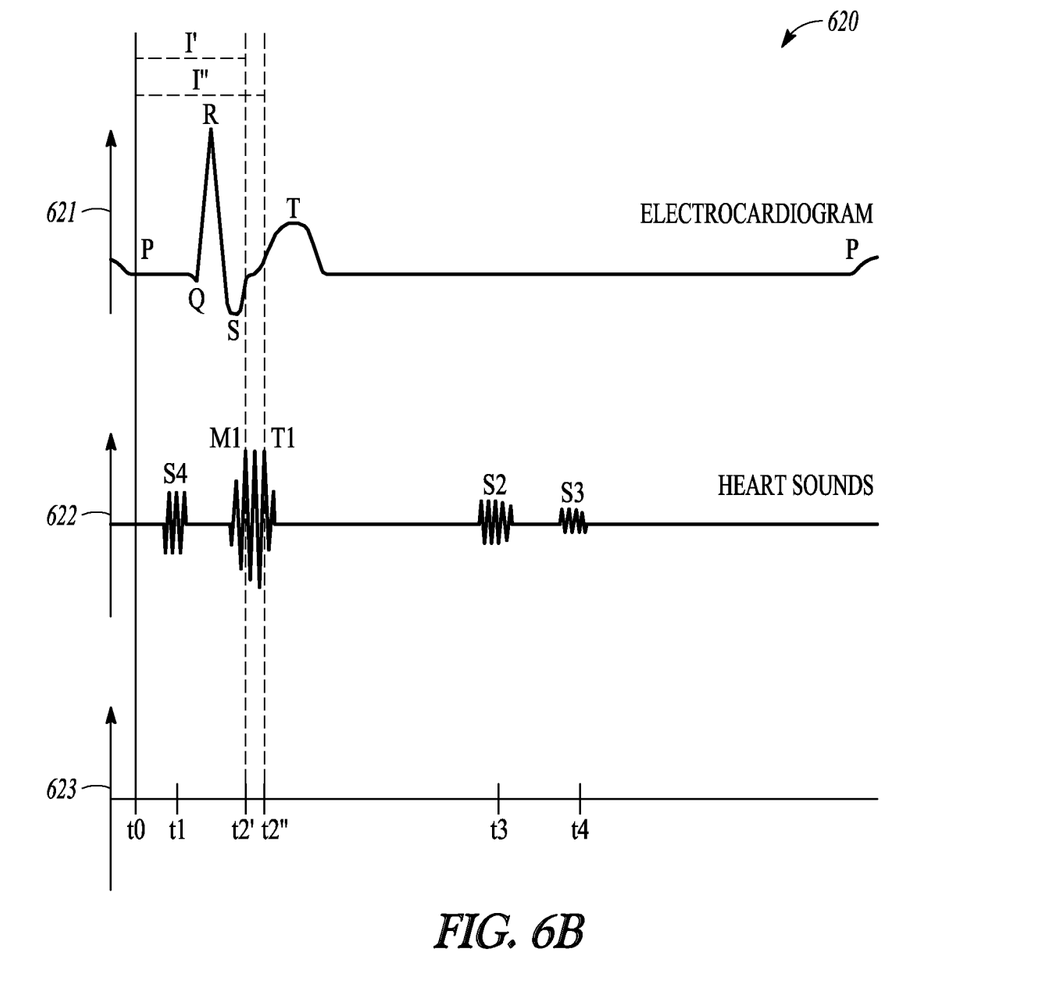

FIGS. 6A and 6B illustrate generally, at 610 and 620 a normal cardiac cycle, and related heart sounds as a function of time. In an example, at 611 or 621 an electrical signal can be detected over time, such as a signal measured using an electrode. The electrical signal 611 or 621 can be indicative of delivery of an electrical stimulation pulse delivered to a patient's heart. In an example, the electrical activation of a patient's heart can be detected by sensing intrinsic depolarization of a patient's heart.

FIGS. 6A and 6B illustrates generally, features of a QRS signal is generally illustrated. A QRS signal can indicate an intrinsic detected event or a paced detected event. In an example, a detected typical electrocardiographic QRS duration 611 can be less than about 100 ms. An atypical electrocardiographic QRS duration 621 can be longer. For example, late pulmonary valve closure, such as can occur in right bundle branch block, can cause an atypical QRS duration 612 of 120 ms or more.

In an example, a mechanical cardiac activity resulting from the electrical activation can be detected over time. A mechanical cardiac activity can be detected by sensing a change in one or more of left ventricular pressure, right ventricular pressure, left atrial pressure, right atrial pressure, systemic arterial pressure, pulmonary artery pressure, by sensing a change in blood flow rate of blood perfusion, by sensing ventricular motion or acceleration, by transthoracically or intrathoracically sensing a change in ventricular impedance, and by sensing a heart sound.

In the example of FIGS. 6A and 6B, mechanical cardiac activity in the form of a heart sound can be detected by sensing acoustic energy. In the example of 612, an acoustic sensor can detect a single S1 heart sound. In the example of 622, atypical heart sounds can be detected, such as an abnormally wide splitting of S1 heart sound caused by delayed tricuspid valve closure, such as can occur in right bundle branch block. In the example of 622, an acoustic sensor can detect an atypical heart, such as the detection of two components of S1 heart sounds, the sound produced by the closure of mitral valve, M1 and the sound produced by the closure of tricuspid valve, T1.

In an example, time intervals can be measured using cardiac activity information, such as electro-mechanical delay information. In an example, a time interval, such as can be indicative of electro-mechanical delay in cardiac function, can be measured between a pacing marker and an indication of opening of the pulmonary valve. In an example, a first time interval can be measured between an initial voltage threshold crossing (e.g., 3 mV) of the electrical signal and the detection of a mechanical cardiac activity event. The time interval can be used as an indication of delay or interval length between a sensed or paced event, and a corresponding physiological response, such as a mechanical cardiac activity indication.

FIGS. 6A and 6B illustrate generally examples 610 and 620 of cardiac activity, and a subject-specific interval determination. In the example of 613 and 623, $t_0$ indicates the time at which an electrical signal crosses an initial voltage threshold (e.g., 1 mV). In the example of 613, subsequent times, such as $t_1$, $t_2$, $t_3$, $t_4$, can correlate with a heart sound, such as S4, S1, S2, and S3, respectively. In the example of 623, $t_2'$ and $t_2''$ can correlate with a heart sound, such as M1 and T1, respectively.

In the example of 610, a subject-specific interval, I, is illustrated between $t_0$ and $t_2$. Time $t_0$ can represent any electrical signal sensed or delivered. Time $t_2$ can represent an arrival of an electrical signal, a physical atrial activation, a pressure change, or other indication of cardiac activity, such as a mechanical event in response to the arrival of an electrical signal, such as an electrical or chemical signal. In response to intrinsic activation of the AV node, a typical delay interval I can be measured as the interval from the end of the pacing event to an indication of a mechanical sense event, such as received heart sound information indicative of ventricular activity. The timing measurement can be taken when a pacing spike occurs in the right ventricle. A time interval can also be measured between $t_0$ and $t_1$, $t_0$ and $t_3$, $t_0$ and $t_4$ or any other interval.

In the example of 620, right bundle block has caused a split S1 sound. A split S1 sound can be common in right bundle block, caused by dyssynchronous closing of the mitral and tricuspid valves. In an example, at 622, the sound produced by the closure of the mitral valve is depicted at M1, and the sound produced by the closure of the tricuspid valve is depicted at T1. In an example, at 623, $t_2'$ corresponds to the time at which a M1 heart sound is detected, and $t_2''$ corresponds to the time at which a T1 heart sound is detected. In the example of 6B, a subject-specific interval, I', is illustrated between $t_0$ and $t_2'$, and subject-specific interval, I'', is illustrated between $t_0$ and $t_2''$.

Pacing can generally be implemented at an interval that is less than I, I', or I'' interval. In an example, stimulation energy can be provided when any one of I, I', or I'' intervals exceeds 100 ms, 105 ms, 110 ms, 115 ms, 120 ms, 125 ms, 130 ms, or any period longer than 130 ms. Using information about the interval, I, I', or I" can provide more efficient cardiac therapy indications. For example, the time interval can be used to determine a therapy based on the timing relationship. A therapy can be one or more of a cardiac pacing therapy, a CRT therapy, a ventricular assist therapy, a defibrillation therapy, a drug delivery therapy, a nerve stimulation therapy, and a ventricular remodeling reversal therapy. A therapy can be based on the time interval to improve the intraventricular or interventricular dyssynchrony of a patient's heart. In another example, stimulation can be delivered using different values and combinations of AV delay, VV delay, pacing site, pacing amplitude or other pacing parameter. The electrical stimulation to mechanical timing (electro-mechanical delay) can be tracked, and the pacing parameter resulting in the shortest or longest electro-mechanical delay can be identified as optimal and can be used to deliver electrostimulation therapy.

In an example, interval information can be obtained to direct therapy. Information regarding one interval or multiple intervals can be obtained. The interval information can direct administration of pacing at a low voltage, such as at 0.5V, for example, and can increase in magnitude until interventricular dyssynchrony is improved. In an example, the magnitude of pacing stimulation energy can be increased, such as in 0.5V increments after every ten beats, until successful intraventricular or interventricular synchronous pacing is observed. The magnitude of the required pacing stimulation energy can depend on a subject's physiology. A subject's physiology can influence the placement of an electrode configured to deliver the pacing stimulating energy. Intraventricular or interventricular synchronous pacing may be achieved with a greater or lesser signal magnitude. Thus, the signal magnitude can be altered based on received interval information.

For example, a cardiac indication can be provided using the interval I, I', I", or similar intervals derived for a particular subject. The cardiac indication can include information about whether a pace event has successfully synchronized intraventricular or interventricular dyssynchrony. In an example, a test interval can be measured beginning at a pacing stimulation energy application time (e.g., Q wave in FIG. 6A), and ending with the detection of mechanical cardiac activity (e.g., $t_2$, $t_2'$, $t_2"$, in FIG. 6B). The test interval can be compared to a subject's previously obtained interval or compared to other test intervals. For example, other test intervals can include intervals describing responses to several pacing stimulation energies.

Figure 7:
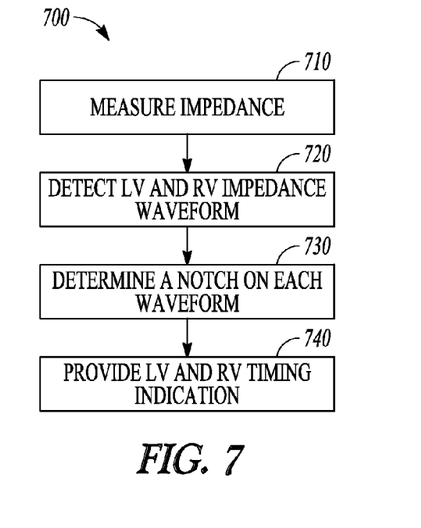
FIG. 7 illustrates generally an example that can include measuring impedance, detecting left ventricular and right ventricular waveform, determining a notch on each waveform, and providing a left ventricular and right ventricular timing indication.

FIG. 7 illustrates generally an example 700 that can include measuring impedance 710, detecting a left ventricular and a right ventricular impedance waveform 720, determining a notch on each waveform 730, and providing a left ventricular and right ventricular timing indication 740. At 700, or any prior or subsequent examples presented herein, the example can be implemented in an IMD programmer device, such as during an IMD implantation procedure. At 700, or any prior or subsequent examples presented herein, the example can be implemented in an IMD and can be adjusted, such as using an external module for periodic testing or patient follow-up.

At 710, an impedance signal can be measured and the occurrence of a notch can be detected in the obtained impedance signal. The impedance signal can be obtained by the mechanical heart signal sensor interface circuit 511, and can be indicative of cardiac function. An impedance measurement can be indicative of the mechanical function of a heart.

At 720, a left ventricular and right ventricular impedance waveform can be detected. The impedance waveform can indicate impedance measurements of cardiac activity, such as indicative of left ventricular and right ventricular wall movement or vibration. The impedance waveform can be provided by the mechanical heart signal sensor interface circuit 511, or any other suitable impedance providing circuit. At least one complete impedance waveform can be collected, or multiple impedance waveforms can be collected to permit averaging of impedance waveforms. Averaging of impedance waveforms can reduce noise. The mechanical heart signal sensor interface circuit can optionally include a filter circuit, such as a Gaussian filter circuit.

At 730, a notch on each waveform can be determined. A notch can occur in an impedance signal where a slope in the impedance signal changes, such as when the slope changes from a positive slope to a negative slope. A notch can be indicated in a predetermined time window during a cardiac cycle. The notch feature can be determined to be the shape of the impedance waveform during a time window following a notch. Any sharp transition in waveform morphology can be determining including a notch, a localized high frequency signal, or abrupt phrase transition, among others.

The optional Gaussian filter discussed above can filter multiple waveforms. For example, a Gaussian can be centered on a notch feature within a waveform. A Gaussian window centered on an S1 measurement can reflect the component of S1 indicative of a valve closure. A Gaussian window centered at a notch on a right valve impedance notch can produce an indication of tricuspid valve closure. A Gaussian window centered at a notch on a left valve impedance notch can produce an indication of mitral valve closure. A Gaussian window centered at a notch on a right valve impedance notch can produce an indication of pulmonary valve opening. A Gaussian window centered at a notch on a left valve impedance notch can produce an indication of aortic valve opening. At least one window in a time-frequency domain can be measured, or more than one window can be measured. More than one window in a time-frequency can focus on more than one frequency, such as a tricuspid component, and a mitral component, among others.

At 740, a left ventricular and right ventricular timing indication can be provided. In an example, when left ventricular and right ventricular walls move in synchrony, the left ventricular and right ventricular wall movements or vibrations can occur in synchrony. When the left ventricle and right ventricle walls move in dyssynchrony, such as in the case of right bundle branch block, the left ventricle and right ventricle wall movements or vibrations can occur at different points in time. An impedance measurement can reflect asynchronous left ventricle and right ventricle movements, such as by determining a notch feature.

Figure 8:
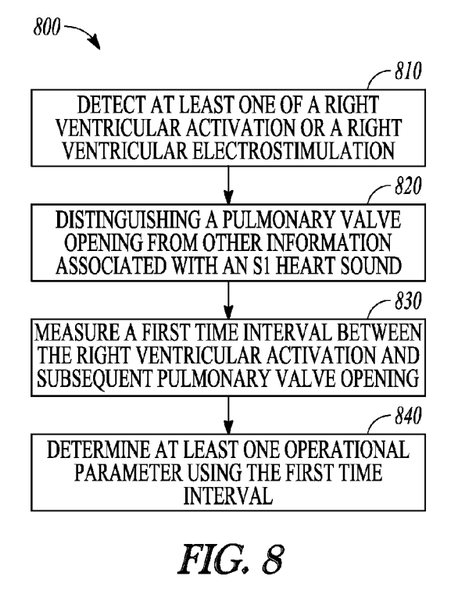
FIG. 8 illustrates generally an example that can include detecting a right ventricular activation or electrostimulation, distinguishing a pulmonary valve opening, measuring a time interval between the right ventricular activation or electrostimulation and a pulmonary valve, and determining at least one operational parameter.

FIG. 8 illustrates generally an example 800 that can include detecting at least one of a right ventricular activation or a right ventricular electrostimulation 810, distinguishing a pulmonary valve opening from other information associated with an S1 heart sound 820, measuring a first time interval between the right ventricular activation and subsequent pulmonary valve opening 830, and determining at least one operational parameter using the first time interval 840.

At 810, a right ventricular activation or a right ventricular electrostimulation information can be received. The right ventricular activation or stimulation information can be provided by a sensor. In an example, the sensor can be configured to provide information to the right ventricular activation circuit 810. A sensor can include a plurality of electrodes configured to measure an electric field. In an example, the plurality of electrodes can be coupled to the processor circuit, such as to monitor an electric field over time.

In an example, the right ventricular activation or the right ventricular electrostimulation information can include electrical information about a physical displacement of cardiac tissue or a blood flow condition inside the heart. For example, right ventricular activation or stimulation information can include electrical information, such as a change in impedance or a change in an electric field. Right ventricular activation or right ventricular electrostimulation information can include electrical signal information, such as electrical signal information sensed using an electrode disposed in a ventricle. For example, right ventricular activation or the right ventricular electrostimulation information can include electrical signal information obtained using an electrode.

At 820, information for distinguishing a pulmonary valve opening from other information associated with an S1 heart sound can be received. The information for distinguishing a pulmonary valve opening from other information associated with an S1 heart sound can be provided by a sensor. In an example, a pressure sensor can be disposed in the thoracic vena cava of a subject to provide a central venous pressure. Information for distinguishing a pulmonary valve opening from other information associated with an S1 heart sound, such as the portion of the cardiac cycle, can be determined using pressure change information, such as central venous pressure change information collected over time. Other pressure sensors can be used to distinguish a pulmonary valve opening, such as an external blood pressure cuff, among others.

A sensor configured to provide information for distinguishing a pulmonary valve opening from other information associated with an S1 heart sound can include an acoustic sensor such as an accelerometer or microphone. The acoustic sensor positioned in or near cardiac tissue can provide information about cardiac tissue displacement, such as to indicate heart sound information, such as S1, M1, T1, S2, S3, or S4.

In an example, information for distinguishing a pulmonary valve opening from other information associated with an S1 heart sound can be received. Distinguishing a pulmonary valve opening from other information associated with an S1 heart sound can include obtaining mechanical information about a physical displacement of cardiac tissue or a blood flow condition inside the heart. For example, distinguishing a pulmonary valve opening time can include obtaining information regarding a particular mechanical motion, such as a contraction. Distinguishing a pulmonary valve opening time can include obtaining information regarding mechanical motion such as contraction or relaxation of a right ventricle or atrium, an opening or closing of a heart valve, such as a pulmonary heart valve, or a physical location change of a portion of cardiac tissue, among others. Distinguishing a pulmonary valve opening time can include obtaining information including blood flow rate information, or pressure information, such as information about a central venous pressure, a right ventricular pressure, or a pulmonary artery pressure, among others.

At 830, a first time interval can be measured between the right ventricular activation and subsequent pulmonary valve opening. In an example, right ventricular activation information can include timing information. Right ventricular activation information can include time interval measurements, such as an interval from a right ventricular activation or a right ventricular electrostimulation to an observed cardiac response, such as a subsequent pulmonary valve opening. A first time interval can include information such as the length of the interval I, I', or I" and the detection of mechanical cardiac activity, such as by a central venous pressure sensor. A first time interval can include information such as the length of the interval I, I', or I" and the detection of electrical activity indicative of cardiac tissue displacement, such as an impedance measurement provided via an electrode disposed in or near the right or left ventricle. In an example, cardiac activity information can include stroke volume timing information over time, such as a time-dependent stroke volume signal, such as can be provided via an intracardiac or intrathoracic impedance measurement.

At 840, at least one operational parameter can be determined, using the first time interval. At least one operational parameter can be generated based on the detection of at least one of a right ventricular activation or a right ventricular electrostimulation, distinguishing a pulmonary valve opening from other information associated with an S1 heart sound. The value can be determined from the measured first time interval between the right ventricular activation and subsequent pulmonary valve opening. At least one operational parameter can provide information, such as information to a cardiac stimulation circuit 110 in the IMD 105.

Figure 9:
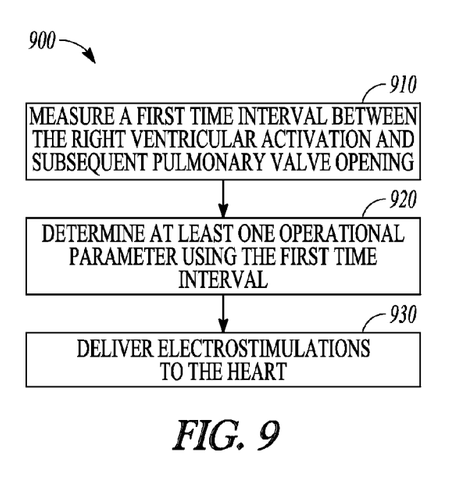
FIG. 9 illustrates generally an example that can include measuring a first time interval, determining at least one operational parameter, and delivering electrostimulations to the heart.

FIG. 9 illustrates generally an example 900 that can include measuring a first time interval between the right ventricular activation and subsequent pulmonary valve opening 910, determining at least one operational parameter using the first time interval 920, and delivering electrostimulations to the heart 930.

At 910, a time interval can be measured or computed, such as from a cardiac electrostimulation time to a time indicative of mechanical cardiac activity. The time interval can include intrinsic cardiac activity information, or cardiac activity information received in response to pacing, such as using the cardiac stimulating circuit 110. In an example, the time interval can be measured or computed according to the discussion above.

At 920, the determined at least one operational parameter using the first time interval can be compared to a threshold value, or to a set of values. For example, a range of intervals expected for conduction of cardiac signal can be established for a particular patient. At 920, a computed time interval can be compared to a threshold time interval.

At 930, electrostimulations can be delivered to the heart. For example, pacing can be delivered to maintain ventricular synchrony and hemodynamic function of the heart. Electrostimulations can include therapy energy generation circuitry (e.g., capacitive, inductive, or other) such as for generating, storing, or delivering an electrostimulation, cardioversion, defibrillation, or other energy.

ADDITIONAL NOTES & EXAMPLES

These non-limiting examples can be combined in any permutation or combination.

Example 1 includes subject matter, such as a system, comprising a cardiac electrical heart signal activation sensing circuit, configured to detect at least one of a right ventricular activation or a right ventricular electrostimulation, and to determine therefrom a corresponding right ventricular activation time. Example 1 can include a cardiac mechanical heart signal sensor interface circuit, configured to distinguish a pulmonary valve opening from other information associated with an S1 heart sound, and to determine therefrom a corresponding subsequent pulmonary valve opening time occurring during the same cardiac cycle. Example 1 can include a timer circuit, coupled to the cardiac electrical heart signal activation circuit and the cardiac mechanical heart signal sensor interface circuit, the timer circuit configured to measure a first time interval between the detected right ventricular activation and the subsequent pulmonary valve opening time occurring during the same cardiac cycle. Example 1 can include a cardiac electrostimulation circuit, coupled to the timer circuit, the cardiac electrostimulation circuit configured to deliver electrostimulations to the heart, the cardiac electrostimulation circuit including at least one operational parameter determined using the first time interval between the detected right ventricular activation and the subsequent pulmonary valve opening time occurring during the same cardiac cycle.

In Example 2, the subject matter of Example 1 can optionally include a cardiac mechanical heart signal sensor interface circuit comprising an impedance feature detector circuit, configured to detect at least one of a right ventricular impedance feature and to provide a corresponding right ventricular impedance feature detection time, or a left ventricular impedance feature and to provide a corresponding left ventricular impedance feature detection time. Example 2 can optionally include a filter circuit, configured to use information about one or more of the right ventricular or left ventricular impedance feature detection times to filter a signal to extract the pulmonary valve opening information.

In Example 3, the subject matter of one or any combination of Examples 1-2 can optionally include a filter circuit configured to receive an acoustic signal including at least one S1 heart sound information, and wherein the filter circuit is configured to use one or more of the right ventricular or left ventricular impedance feature detection times to define at least one window of the acoustic signal from which to extract the pulmonary valve opening information.

In Example 4, the subject matter of one or any combination of Examples 1-3 can optionally include a filter circuit configured to define the at least one window in a time-frequency domain.

In Example 5, the subject matter of one or any combination of Examples 1-4 can optionally include a filter circuit configured to compare timing of the left ventricular impedance feature with respect to timing of the right ventricular impedance feature to extract the pulmonary valve opening information.

In Example 6, the subject matter of one or any combination of Examples 1-5 can optionally include a filter circuit configured to provide a Gaussian filter characteristic, centered at the at least one window of the acoustic signal, from which to extract the pulmonary valve opening information.

In Example 7, the subject matter of one or any combination of Examples 1-6 can optionally include a filter circuit configured to provide the Gaussian filter characteristic, centered at the at least one window of the acoustic signal, from which to extract the aortic valve opening information.

In Example 8, the subject matter of one or any combination of Examples 1-7 can optionally include a filter circuit configured to provide the Gaussian filter characteristic, centered at the at least one window of the acoustic signal, from which to extract the tricuspid valve opening information.

In Example 9, the subject matter of one or any combination of Examples 1-8 can optionally include a filter circuit is configured to receive a blood pressure signal from which to extract the pulmonary valve opening information.

In Example 10, the subject matter of one or any combination of Examples 1-9 can optionally include a filter circuit configured to receive a blood flow signal from which to extract the pulmonary valve opening information.

Example 11 can include, or can be combined with the subject matter of one or any combination of Examples 1-10 to optionally include subject matter (such as a method, a means for performing acts, or a machine-readable medium including instructions that, when performed by the machine, cause the machine to perform acts) that can include detecting at least one of a right ventricular activation or a right ventricular electrostimulation, and determining therefrom a corresponding right ventricular activation time. Example 11 can optionally include distinguishing a pulmonary valve opening from other information associated with an S1 heart sound, and determining therefrom a corresponding subsequent pulmonary valve opening time occurring during the same cardiac cycle. Example 11 can optionally include measuring a first time interval between the detected right ventricular activation and the subsequent pulmonary valve opening time occurring during the same cardiac cycle. Example 11 can optionally include determining at least one operational parameter using the first time interval between the detected right ventricular activation and the subsequent pulmonary valve opening time occurring during the same cardiac cycle. Example 11 can optionally include delivering electrostimulations to the heart.

In Example 12, the subject matter of one or any combination of Examples 1-11 can optionally include distinguishing a pulmonary valve opening including detecting at least one of a right ventricular impedance feature and providing a corresponding right ventricular impedance feature detection time or a left ventricular impedance feature and providing a corresponding left ventricular impedance feature detection time. Example 12 can optionally include using information about one or more of right ventricular or left ventricular impedance feature detection times and filtering a signal to extract the pulmonary valve opening information.

In Example 13, the subject matter of one or any combination of Examples 1-12 can optionally include filtering a signal to extract the pulmonary valve opening information including receiving an acoustic signal including at least one S1 heart sound information, and using one or more of the right ventricular or left ventricular impedance feature detection times to define at least one window of the acoustic signal from which to extract the pulmonary valve opening information.

In Example 14, the subject matter of one or any combination of Examples 1-13 can optionally include filtering a signal to extract the pulmonary valve opening information including defining the at least one window in a time-frequency domain.

In Example 15, the subject matter of one or any combination of Examples 1-14 can optionally include filtering a signal to extract the pulmonary valve opening information including comparing timing of the left ventricular impedance feature with respect to timing of the right ventricular impedance feature to extract the pulmonary valve opening information.

In Example 16, the subject matter of one or any combination of Examples 1-15 can optionally include filtering a signal to extract the pulmonary valve opening information including providing a Gaussian filter characteristic, centered at the at least one window of the acoustic signal, from which to extract the pulmonary valve opening information.

In Example 17, the subject matter of one or any combination of Examples 1-16 can optionally include providing a Gaussian filter characteristic, centered at the at least one window of the acoustic signal including obtaining the right ventricular impedance feature.

In Example 18, the subject matter of one or any combination of Examples 1-17 can optionally include providing a Gaussian filter characteristic, centered at the at least one window of the acoustic signal including obtaining the left ventricular impedance feature.

In Example 19, the subject matter of one or any combination of Examples 1-18 can optionally include filtering a signal to extract the pulmonary valve opening information including receiving a blood pressure signal or a blood flow signal from which to extract the pulmonary valve opening information.

Example 20 can include, or can be combined with the subject matter of one or any combination of Examples 1-19 to optionally include subject matter such as a system comprising a cardiac electrical heart signal activation sensing circuit, configured to detect at least one of a right ventricular activation or a right ventricular electrostimulation, and to determine therefrom a corresponding right ventricular activation time. Example 20 can optionally include an impedance feature detector circuit, configured to detect at least one of a right ventricular impedance feature and to provide a corresponding right ventricular impedance feature detection time, or a left ventricular impedance feature and to provide a corresponding left ventricular impedance feature detection time. Example 20 can optionally include a filter circuit, configured to use information about one or more of the right ventricular or left ventricular impedance feature detection times to filter a signal to extract the pulmonary valve opening information. Example 20 can optionally include a timer circuit, coupled to the cardiac electrical heart signal activation circuit and the impedance feature detector circuit, the timer circuit configured to measure a first time interval between the detected right ventricular impedance feature and the filtered pulmonary valve opening information. Example 20 can optionally include a cardiac electrostimulation circuit, coupled to the timer circuit, the cardiac electrostimulation circuit configured to deliver electrostimulations to the heart, the cardiac electrostimulation circuit including at least one operational parameter determined using the first time interval between the detected right ventricular impedance feature and the filtered pulmonary valve opening information during the same cardiac cycle.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   a cardiac electrical heart signal activation sensing circuit, configured to detect at least one of a right ventricular activation or a right ventricular electrostimulation, and to determine therefrom a corresponding right ventricular activation time for a first cardiac cycle;
   a cardiac mechanical heart signal sensor interface circuit, configured to use information about an S1 heart sound to distinguish a pulmonary valve opening from other information associated with the S1 heart sound, and to determine therefrom a pulmonary valve opening time occurring during the same first cardiac cycle;
   a timer circuit, coupled to the cardiac electrical heart signal activation circuit and the cardiac mechanical heart signal sensor interface circuit, the timer circuit configured to measure a first time interval between the detected right ventricular activation and the pulmonary valve opening time occurring during the same first cardiac cycle; and
   a cardiac electrostimulation circuit, coupled to the timer circuit, the cardiac electrostimulation circuit configured to deliver electrostimulations to the heart, the cardiac electrostimulation circuit including at least one operational parameter determined using the first time interval between the detected right ventricular activation and the pulmonary valve opening time occurring during the same first cardiac cycle.

2. The system of claim 1, wherein the cardiac electrical heart signal activation sensing circuit comprises:
an impedance feature detector circuit, configured to detect at least one of:
a right ventricular impedance feature and to provide a corresponding right ventricular impedance feature detection time; or
a left ventricular impedance feature and to provide a corresponding left ventricular impedance feature detection time; and
a filter circuit, configured to use information about one or more of the right ventricular or left ventricular impedance feature detection times to filter a signal to extract the pulmonary valve opening information.

3. The system of claim 2, wherein the filter circuit is configured to receive an acoustic signal including S1 heart sound information, and wherein the filter circuit is configured to use one or more of the right ventricular or left ventricular impedance feature detection times to define at least one window of the acoustic signal from which to extract the pulmonary valve opening information.

4. The system of claim 3, wherein the filter circuit is configured to define the at least one window in a time-frequency domain.

5. The system of claim 4, wherein the filter circuit is configured to compare timing of the left ventricular impedance feature with respect to timing of the right ventricular impedance feature to extract the pulmonary valve opening information.

6. The system of claim 3, wherein the filter circuit is configured to provide a Gaussian filter characteristic, centered at the at least one window of the acoustic signal, from which to extract the pulmonary valve opening information.

7. The system of claim 6, wherein the filter circuit is configured to provide the Gaussian filter characteristic, centered at the at least one window of the acoustic signal, from which to extract the aortic valve opening information.

8. The system of claim 6, wherein the filter circuit is configured to provide the Gaussian filter characteristic, centered at the at least one window of the acoustic signal, from which to extract the tricuspid valve opening information.

9. The system of claim 3, wherein the filter circuit is configured to receive a blood pressure signal from which to extract the pulmonary valve opening information.

10. The system of claim 3, wherein the filter circuit is configured to receive a blood flow signal from which to extract the pulmonary valve opening information.

11. A method comprising:
detecting at least one of a right ventricular activation or a right ventricular electrostimulation, and determining therefrom a corresponding right ventricular activation time for a first cardiac cycle;
using information about an S1 heart sound from a cardiac mechanical activity sensor, distinguishing a pulmonary valve opening from other information associated with the S1 heart sound, and determining therefrom a pulmonary valve opening time occurring during the same first cardiac cycle;
measuring a first time interval between the detected right ventricular activation and the pulmonary valve opening time occurring during the same first cardiac cycle;
determining at least one operational parameter for a cardiac electrostimulation device using the first time interval between the detected right ventricular activation and the pulmonary valve opening time occurring during the same first cardiac cycle.

12. The method of claim 11, wherein the distinguishing a pulmonary valve opening includes:
detecting at least one of:
a right ventricular impedance feature and providing a corresponding right ventricular impedance feature detection time; or
a left ventricular impedance feature and providing a corresponding left ventricular impedance feature detection time; and
using information about one or more of the right ventricular or left ventricular impedance feature detection times and filtering a signal to extract the pulmonary valve opening information.

13. The method of claim 12, wherein the filtering a signal to extract the pulmonary valve opening information includes receiving an acoustic signal including at least one S1 heart sound information, and using one or more of the right ventricular or left ventricular impedance feature detection times to define at least one window of the acoustic signal from which to extract the pulmonary valve opening information.

14. The method of claim 13, wherein the filtering a signal to extract the pulmonary valve opening information includes defining the at least one window in a time-frequency domain.

15. The method of claim 14, wherein the filtering a signal to extract the pulmonary valve opening information includes comparing timing of the left ventricular impedance feature with respect to timing of the right ventricular impedance feature to extract the pulmonary valve opening information.

16. The method of claim 13, wherein the filtering a signal to extract the pulmonary valve opening information includes providing a Gaussian filter characteristic, centered at the at least one window of the acoustic signal, from which to extract the pulmonary valve opening information.

17. The method of claim 16, wherein the providing a Gaussian filter characteristic, centered at the at least one window of the acoustic signal includes obtaining the right ventricular impedance feature.

18. The method of claim 16, wherein the providing a Gaussian filter characteristic, centered at the at least one window of the acoustic signal includes obtaining the left ventricular impedance feature.

19. The method of claim 13, wherein the filtering a signal to extract the pulmonary valve opening information includes receiving a blood pressure signal or a blood flow signal from which to extract the pulmonary valve opening information.

20. A system comprising:
a cardiac electrical heart signal activation sensing circuit, configured to detect at least one of a right ventricular activation or a right ventricular electrostimulation, and to determine therefrom a corresponding right ventricular activation time;
an impedance feature detector circuit, configured to detect at least one of:
a right ventricular impedance feature and to provide a corresponding right ventricular impedance feature detection time; or
a left ventricular impedance feature and to provide a corresponding left ventricular impedance feature detection time;
a filter circuit, configured to use information about one or more of the right ventricular or left ventricular impedance feature detection times to filter a signal to extract the pulmonary valve opening information;

a timer circuit, coupled to the cardiac electrical heart signal activation circuit and the impedance feature detector circuit, the timer circuit configured to measure a first time interval between the detected right ventricular impedance feature and the filtered pulmonary valve opening information; and a cardiac electrostimulation circuit, coupled to the timer circuit, the cardiac electrostimulation circuit configured to deliver electrostimulations to the heart, the cardiac electrostimulation circuit including at least one operational parameter determined using the first time interval between the detected right ventricular impedance feature and the filtered pulmonary valve opening information during the same cardiac cycle.

\* \* \* \* \*